US011278449B2

(12) United States Patent
Ryan

(10) Patent No.: US 11,278,449 B2
(45) Date of Patent: Mar. 22, 2022

(54) DYNAMIC SUPPORT FOR OPHTHALMIC DEVICE

(71) Applicant: Edwin Ryan, St. Paul, MN (US)

(72) Inventor: Edwin Ryan, St. Paul, MN (US)

(73) Assignee: Edwin Ryan, St. Paul, MN (US)

(*) Notice: Subject to any disclaimer, the term of this patent is extended or adjusted under 35 U.S.C. 154(b) by 332 days.

(21) Appl. No.: 15/762,992

(22) PCT Filed: Sep. 23, 2016

(86) PCT No.: PCT/US2016/053492
§ 371 (c)(1),
(2) Date: Mar. 23, 2018

(87) PCT Pub. No.: WO2017/053832
PCT Pub. Date: Mar. 30, 2017

(65) Prior Publication Data
US 2018/0214307 A1 Aug. 2, 2018

Related U.S. Application Data

(60) Provisional application No. 62/232,898, filed on Sep. 25, 2015.

(51) Int. Cl.
*A61F 9/007* (2006.01)
*A61B 17/34* (2006.01)
(Continued)

(52) U.S. Cl.
CPC .......... *A61F 9/00763* (2013.01); *A61B 17/34* (2013.01); *A61F 9/00736* (2013.01);
(Continued)

(58) Field of Classification Search
CPC .. A61F 9/00763; A61F 9/00736; A61F 9/007; A61B 17/34; A61B 2090/062;
(Continued)

(56) References Cited

U.S. PATENT DOCUMENTS 4,530,359 A * 7/1985 Helfgott .............. A61F 9/00754
30/362
5,547,473 A 8/1996 Peyman
(Continued)

FOREIGN PATENT DOCUMENTS

CN 103037802 A 4/2013
CN 108697413 A 10/2018
(Continued)

OTHER PUBLICATIONS

International Application Serial No. PCT/US2016/053492, International Search Report and Written Opinion dated Dec. 8, 2016, 8 pgs.
(Continued)

*Primary Examiner* — Erich G Herbermann
(74) *Attorney, Agent, or Firm* — Schwegman Lundberg & Woessner, P.A.

(57) ABSTRACT

A small gauge surgical instrument is shown with advantages such as diminished "play" at the tip. A surgical instrument assembly is also shown with support along a length of the instrument that can be selected by the surgeon. Devices and method described provide adjustability of the instrument without protruding into a gripping surface of the instrument.

11 Claims, 3 Drawing Sheets

(51) Int. Cl.
    *A61B 17/00*     (2006.01)
    *A61B 90/00*     (2016.01)
(52) U.S. Cl.
    CPC .............. *A61B 2017/00544* (2013.01); *A61B 2017/3407* (2013.01); *A61B 2017/3492* (2013.01); *A61B 2090/062* (2016.02); *A61B 2090/0811* (2016.02); *A61F 9/007* (2013.01)
(58) Field of Classification Search
    CPC .. A61B 2090/0811; A61B 2017/00544; A61B 2017/3407; A61B 2017/3492
    See application file for complete search history.

(56) References Cited

U.S. PATENT DOCUMENTS

| | | | |
|---|---|---|---|
| 2006/0089607 | A1 | 4/2006 | Chen |
| 2010/0010452 | A1* | 1/2010 | Paques ............... A61F 9/0017 604/192 |
| 2012/0078224 | A1 | 3/2012 | Lerner et al. |
| 2013/0178822 | A1* | 7/2013 | Hickingbotham ...... A61K 35/30 604/506 |

FOREIGN PATENT DOCUMENTS

| | | | | |
|---|---|---|---|---|
| EP | 3352682 | A1 | 8/2018 | |
| EP | 3352682 | B1 | 7/2020 | |
| IN | 201817014945 | A | 9/2018 | |
| JP | 2009072221 | A | 4/2009 | |
| JP | 2010515504 | A | 5/2010 | |
| JP | 2018529498 | A | 10/2018 | |
| WO | WO-2010064670 | A1 * | 6/2010 | ......... A61F 9/00736 |
| WO | WO-2010064670 | A1 | 6/2010 | |
| WO | WO-2012135109 | A1 | 10/2012 | |
| WO | WO-2014035862 | A1 * | 3/2014 | ........... A61F 9/0008 |

OTHER PUBLICATIONS

Brazilian Application Serial No. BR1120180060569, Voluntary Amendment filed Sep. 20, 2019, w/ English Claims, 30 pgs.
European Application Serial No. 16849775.8, Extended European Search Report dated Oct. 1, 2018, 7 pgs.
European Application Serial No. 16849775.8, Response filed Feb. 28, 2019 to Extended European Search Report dated Oct. 1, 2018, 20 pgs.
International Application Serial No. PCT/US2016/053492, International Preliminary Report on Patentability dated Apr. 5, 2018, 8 pgs.
Australian Application Serial No. 2016326682, First Examination Report dated Jul. 1, 2020, 5 pgs.
Brazilian Application Serial No. BR1120180060569, Office Action dated May 31, 2020, w/ English Translation, 5 pgs.
Chinese Application Serial No. 201680068686.5, Office Action dated Jun. 1, 2020, w/ English Translation, 17 pgs.
Brazilian Application Serial No. BR1120180060569, Response filed Sep. 4, 2020 to Office Action dated May 31, 2020, w/ English Claims, 13 pgs.
Chinese Application Serial No. 201680068686.5, Office Action dated Dec. 14, 2020, w/ English translation, 13 pgs.
Chinese Application Serial No. 201680068686.5, Response fied Sep. 30, 2020 to Office Action dated Jun. 1, 2020, w/ English Claims, 7 pgs.
Chinese Application Serial No. 201680068686.5, Response filed Mar. 1, 2021 to Office Action dated Dec. 14, 2020, w/ English claims, 5 pgs.
Japanese Application Serial No. 2018-536067, Notification of Reasons for Refusal dated Sep. 15, 2020, w/ English translation, 8 pgs.
Japanese Application Serial No. 2018-536067, Response filed Mar. 5, 2021 to Notification of Reasons for Refusal dated Sep. 15, 2020, w/ English claims, 6 pgs.
Australian Application Serial No. 2016326682, Response filed Apr. 1, 2021 to First Examination Report dated Jul. 1, 2020, 11 pgs.
Chinese Application Serial No. 201680068686.5, Office Action dated Apr. 6, 2021, w/ English Translation, 13 pgs.
Indian Application Serial No. 201817014945, First Examination Report dated May 29, 2021, 6 pgs.
Canadian Application Serial No. 2,999,874, Office Action dated Oct. 5, 2021, 5 pgs.
Chinese Application Serial No. 201680068686.5, Response filed Jun. 21, 2021 to Office Action dated Apr. 6, 2021, w/ English claims, 6 pgs.
Chinese Application Serial No. 201680068686.5, Decision of Rejection dated Jan. 4, 2022, w/ English translation, 13 pgs.

* cited by examiner

DYNAMIC SUPPORT FOR OPHTHALMIC DEVICE

CLAIM OF PRIORITY

This application is a U.S. National Stage Filing under 35 U.S.C. 371 from International Application No. PCT/US2016/053492, filed on Sep. 23, 2016, and published as WO 2017/053823 A1 on Mar. 30, 2017, which claims the benefit of priority to U.S. Provisional Patent Application Ser. No. 62/232,898, filed on Sep. 25, 2015, each of which is incorporated by reference herein in its entirety.

TECHNICAL FIELD

This invention relates to small gauge instruments typically used for surgical procedures such as surgery of the eye.

BACKGROUND

Ophthalmological surgery continues to evolve towards smaller instruments that produce smaller incisions. The most common incision size currently is 25 gauge, but newer instruments as small as 27 gauge (approximately 0.41 mm diameter) are being utilized, and smaller instruments are likely in the future. The advantages of smaller incisions are multiple, including lessened trauma, faster healing, faster wound management (no sutures), and greater patient comfort.

Problems exist with the smaller instruments, however. The small diameter of the instruments makes them quite flexible, which is a disadvantage for the surgeon. With larger diameter instruments, there is very little "play", so the tips of the instruments go exactly where the surgeon desires that they go. With the smaller diameter instruments, the tips can move from their intended positions due to the bending or flexing of the fine wire-like instruments, which makes the surgeon feel a loss of control.

Bending or flexing of the small instruments is of particular concern in some procedures, for example, removal of peripheral vitreous, when the eye must be turned to allow viewing by the surgeon. Turning of the eye is accomplished by moving the instrument relative to the patient's head while a portion of the instrument remains inserted within a portion of the eye. Because the amount of flexing of the instrument is relatively large and unpredictable to the surgeon, precise repositioning of the eye becomes more difficult. In addition, delicate maneuvers such as peeling membranes from the retinal surface become significantly more difficult when instruments are too flexible causing imprecision of movements.

What is needed is an instrument design that accommodates increasingly small diameters, and still provides precise control without unwanted flexing.

Overview

The present instruments, and related methods provide means for diminishing the "play" in very small and flexible instruments, such as instruments for ophthalmological surgery. Embodiments described include designs where characteristics such as stiffness can be adjusted by a surgeon. Embodiments described also include adjustments so access is possible to all parts of the vitreous cavity. Embodiments described also include an adjustment mechanism where a level of support of a small diameter instrument can be varied, yet a number of supply lines remain located in a central part of a base unit, and the support frame is contained within a substantially continuous gripping surface of the base unit.

DETAILED DESCRIPTION

Figure 1:
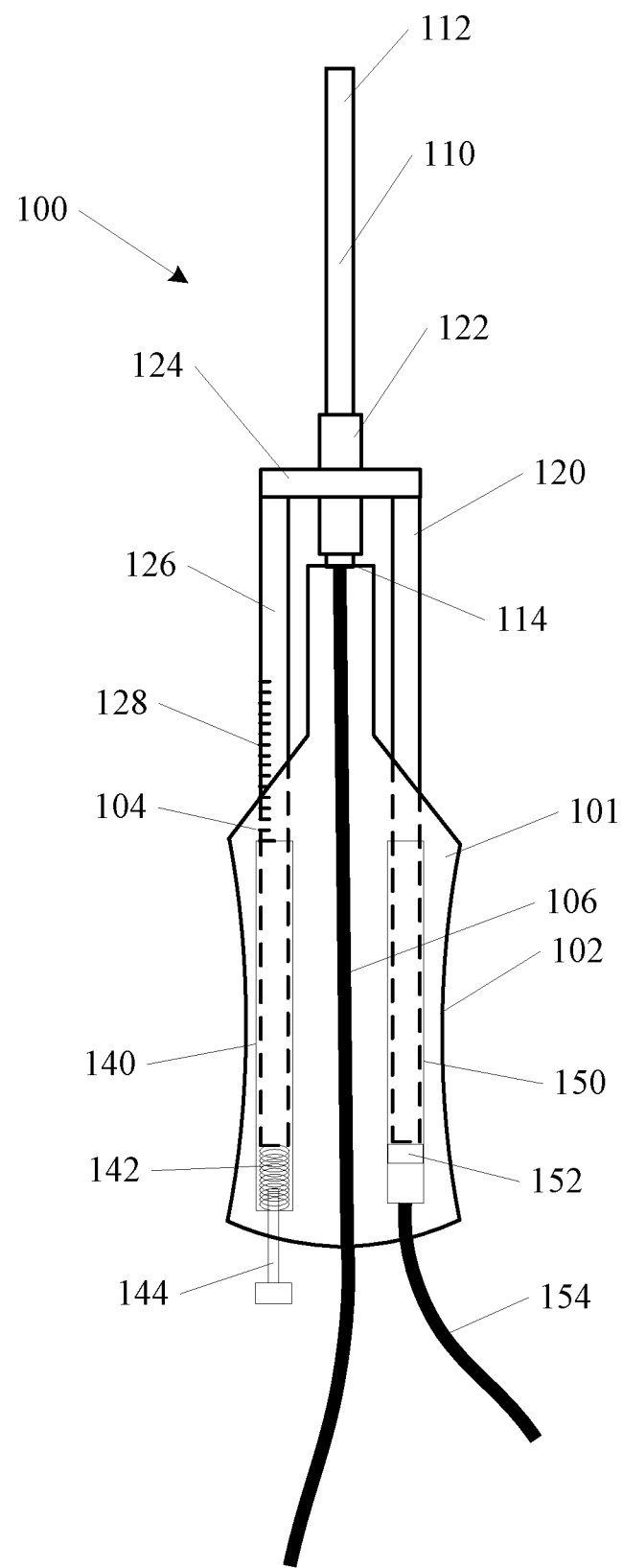
FIG. 1 shows a side view of an instrument according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, or logical changes, etc. may be made without departing from the scope of the present invention.

FIG. 1 shows an instrument 100 including a small diameter instrument 110, and a support device 120. The small diameter instrument 110 includes a distal end 112 and a proximal end 114. In one example, the small diameter instrument 110 includes a hollow tube. In one example, the small diameter instrument 110 has a diameter smaller than 20 gauge. In one example, the small diameter instrument 110 has a diameter equal to, or smaller than 23 gauge. In one example, the small diameter instrument 110 has a diameter of approximately 25 gauge. In one example, the small diameter instrument 110 has a diameter of approximately 27 gauge.

The small diameter instrument 110 is shown extending from a base unit 101. The base unit 101 includes a lateral gripping surface 102. During a procedure, it is desirable to have the gripping surface 102 free from protrusions, or controls that may interfere with a surgeon's grip of the base unit 101. In one example, the base unit 101 is configured to be the same size and shape of a base unit in existing ophthalmological devices. It is desirable to make the base unit 101 of the present disclosure move and feel the same as existing base units, with added features, such as adjustable support.

One or more supply lines 106 are shown extending into the base unit 101 and routed through an interior of the base unit 101. In one example, one or more of the supply lines 106 includes a fiber optic supply line, such as general illumination, or a laser for drug activation, cauterization, ablation, etc. In one example, one or more of the supply lines 106 includes a passage for infusion of a media such as liquid, gas, or supply of a drug, or a passage for suction of material. In one example, one or more of the supply lines 106 includes an introducer for an instrument such as a cutting tool (e.g. scissors, blade, etc.) or other tools such as forceps, probes, etc.

In one example, one or more of the supply lines 106 includes a pneumatic supply line. In one pneumatic supply line example, pneumatic pressure may be used to power a reciprocating vitrectomy blade. In one pneumatic supply line example, pneumatic pressure may be used to provide a dynamic bias to the support device 120 as described in examples below. In one example, a single supply line 106 provides pneumatic pressure to power more than one function, such as a reciprocating vitrectomy blade and a dynamic bias to the support device 120.

In one example, it is desirable to route supply lines through approximately a center of the base unit 101 for ease of manufacture, and ease of use. Configurations described below provide adjustable properties of the instrument 100 to the surgeon without affecting location of the supply lines 106, or protruding outside of the lateral gripping surface 102. In one example, the lateral gripping surface 102 is continuous, with no interruptions in the lateral gripping surface 102 that may interfere with gripping comfort to a user.

The small diameter instrument 110 and the support device 120 are movable relative to each other, allowing the user to vary an amount of support provided by the support device 120 to the small diameter instrument 110. In one example, a support device 120 of adequate stiffness is positioned along the shaft of the small diameter instrument 110 (25 gauge, 27 gauge, or the like). The support device 120 stabilizes the instrument so the surgeon using it has a greater sense of security regarding the position of the tip inside the eye. The support device 120 is variable so that the full length of the small diameter instrument 110 can be selectively inserted into the eye for posterior work. Posterior work typically requires minimal twisting motion by the surgeon, therefore a lower need for stabilization.

Although "gauge" is used to define a size of the small diameter instrument, the invention is not limited to circular cross section instruments. When referring to non-circular small diameter instruments, an average diameter can be used to define a gauge.

For a procedure that will benefit from more support, such as a peripheral vitrectomy, the support device 120 can be positioned down the shaft of the small diameter instrument 110 to provide increased support. With the support device 120 moved closer to the distal end 112, less play is present at the distal end 112 of the small diameter instrument 110 when the eye is twisted and turned by the surgeon.

In one example, the support device 120 design includes a sliding portion 122 having a close tolerance fit with the small diameter instrument 110, to allow adjustment of support, while minimizing lateral motion of the small diameter instrument 110 within the sliding portion 122. In one example, a 20 gauge cylinder is used as a sliding portion 122. The sliding portion 122 may be constructed of a strong material such as stainless steel, to go around the small diameter instrument 110. The sliding portion 122 is attached to an adjustment mechanism, including one or more rods 126 that runs parallel to the small diameter instrument 110. In one example the sliding portion 122 is attached to the rods 126 using a coupling member 124. FIG. 1 shows the rods 126 slidably moving within holes 104 in the base unit 101.

In one example, a scale 128 such as gradated lines, or other indicia are included to indicate a relative position of the sliding portion 122 with respect to the length of the small diameter instrument 110. Examples that include the scale 128 provide an indication of the different levels of lateral support provided to the small diameter instrument 110.

The example instrument 100 from FIG. 1 further includes a biasing device 140. In one example, the biasing device 140 is actuated by a spring 142. In operation, a biasing device urges the support device 120 towards an extended location along the length of the small diameter instrument 110. Additionally, the biasing device 140 provides a force to urge at least a distal portion of the support device 120 against an eye of a patient during a procedure.

The small diameter instrument 110 is permitted to move freely within the support device 120 and into the patient's eye to a depth as desired by the surgeon. The surgeon selects the desired depth within the eye merely be pushing the small diameter instrument 110 into, or out of, the eye. Concurrently, the support frame is pressed by the biasing device 140 to maintain contact with the outer surface of the eye. In this way, a maximum amount of lateral support is provided to the small diameter instrument 110 by the support device 120, while the small diameter instrument 110 is the only instrument to actually enter the eye, thus reducing the size of the incision.

Another example of a biasing device 150 is shown in FIG. 1. The biasing device 150 includes a piston 152 adapted to be biased by pneumatic pressure. A pneumatic line 154 is shown coupled to the biasing device 150 to provide the necessary pressure.

Although a separate pneumatic line 154 is shown in FIG. 1 coupled to the biasing device 150, the invention is not so limited. In one example, the instrument 100 is coupled to a single pneumatic line that is used for multiple functions. One example includes a single pneumatic line to power both a reciprocating vitrectomy blade and the biasing device 150.

FIG. 1 shows two examples of possible biasing devices 140, 150 in a single instrument 100 to illustrate multiple possibilities for biasing devices. In practical application, a single type of biasing device will be most cost effective, although having multiple types of biasing devices is certainly possible. Additionally, although spring and pneumatic biasing devices are shown, the invention is not so limited. Other types of biasing devices include, but are not limited to, hydraulic biasing devices, elastomer actuated biasing devices, and other biasing mechanisms.

In one example a biasing force of the biasing device 140, 150 is adjustable. For example, a regulator may be used with biasing device 150 to adjust an amount of force, or a screw adjuster 144 may be used to set a preload amount on the spring 142 in the biasing device 140. In other examples, a biasing force may be determined at manufacture of the instrument 100, and may not be adjustable by the surgeon.

Figure 2:
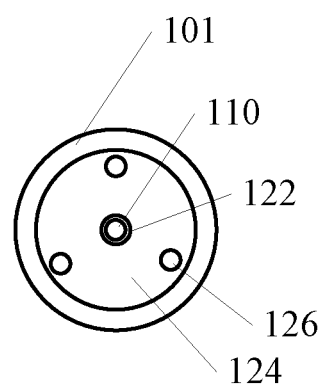
FIG. 2 shows a top view of the instrument from FIG. 1, according to an embodiment of the invention.

FIG. 2 shows an end view of the instrument 100 from FIG. 1. The small diameter instrument 110, with the sliding portion 122 is shown in approximately the center of the base unit 101. The rods 126 are shown coupled to the sliding portion 122 by the coupling member 124. The example shown in FIG. 2 illustrates a solid disk shaped coupling member 124, however one of ordinary skill in the art, having the benefit of the present disclosure, will recognize that other configurations such as struts, or complex shaped coupling members 124 are within the scope of the invention.

Three approximately equally spaced rods 126 are shown in FIG. 2, although other numbers of rods 126 are within the scope of the invention. Three substantially equally spaced rods are a stable configuration, providing support on three axes for increased stability and control.

Figure 3A:
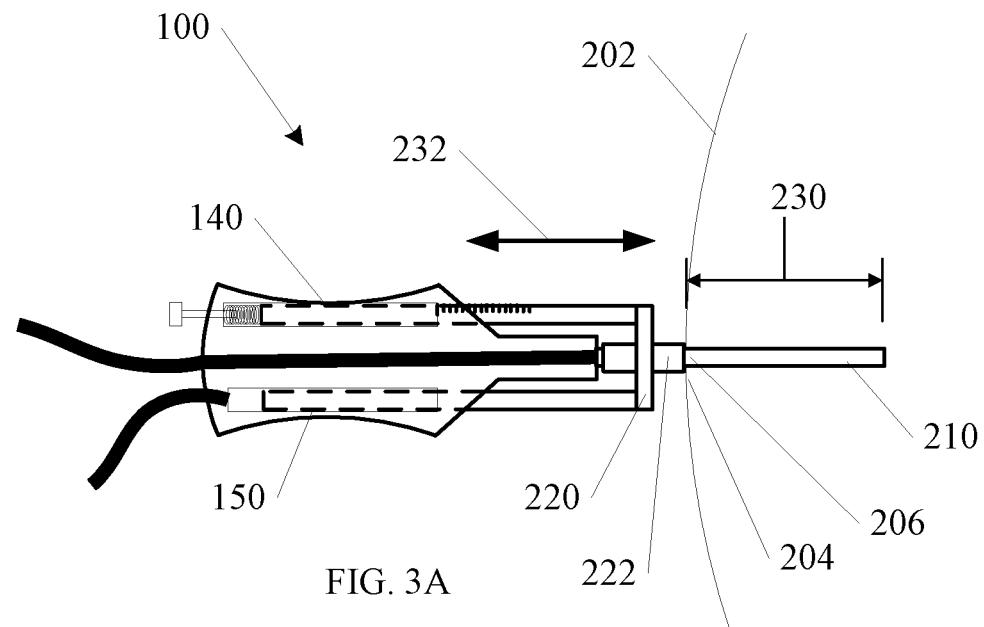
FIG. 3A shows a side view of an instrument in use according to an embodiment of the invention.
Figure 3B:
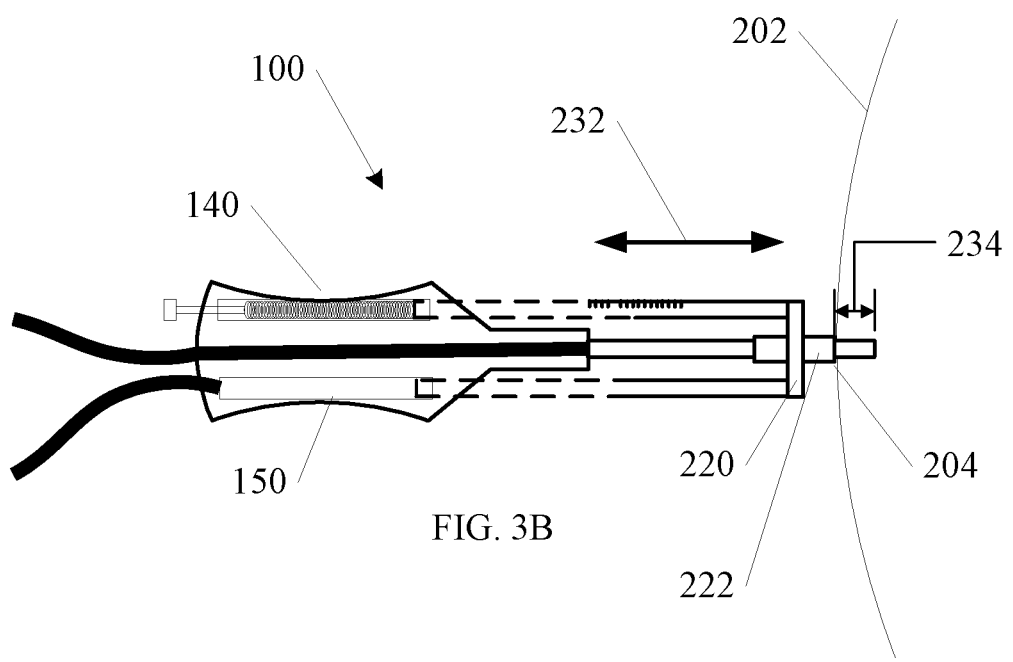
FIG. 3B shows another side view of an instrument in use according to an embodiment of the invention.

FIGS. 3A and 3B show examples of instrument 100 in use. In FIG. 3A, a small diameter instrument 210 is inserted into an incision 206 in an eye. An outer surface 202 of the eye is contacted with a distal portion 222 of a support frame 220. As the small diameter instrument 210 is inserted into the incision 206, it is allowed to slide freely within the support frame 220 and into the eye. In FIG. 3A, the small diameter instrument 210 moves along direction 232 to a depth 230 within the eye.

The distal portion 222 of the support frame 220 is biased against the surface 202 of the eye by one or more biasing device, such as biasing devices 140, 150. As discussed above, the distal portion 222 is pressed by the biasing device to maintain contact with the outer surface 202 of the eye. In this way, a maximum amount of lateral support is provided to the small diameter instrument 210 by the support device 220.

In FIG. 3B, the instrument 100 is moved away from the eye along direction 232, and as a result the small diameter instrument 210 is retracted to a more shallow depth 234. Due to the one or more biasing devices, the distal portion 222 remains pressed to maintain contact with the outer surface 202 of the eye, and the support frame 220 provides a maximum amount of lateral support to the small diameter instrument 210 while keeping the small incision 206, and only allowing the small diameter instrument 210 within the eye.

In one example, the configuration shown in FIG. 3B may be used to rotate the eye during a procedure. With the shallow depth 234 of the small diameter instrument 210, a large amount of lateral support is being provided, and side to side motion of the instrument 100 will not cause large deflections in the tip of the small diameter instrument 210. After the eye is rotated to a desired orientation, the small diameter instrument 210 may be re-inserted to the depth 230 as shown in FIG. 3A.

As shown in the examples provided, a level of support of the small diameter instrument can be varied, yet the number of supply lines remain located in a central part of the base unit, and the support frame is contained within a substantially continuous gripping surface of the base unit. No adjustment controls protrude through the substantially continuous gripping surface.

Figure 4:
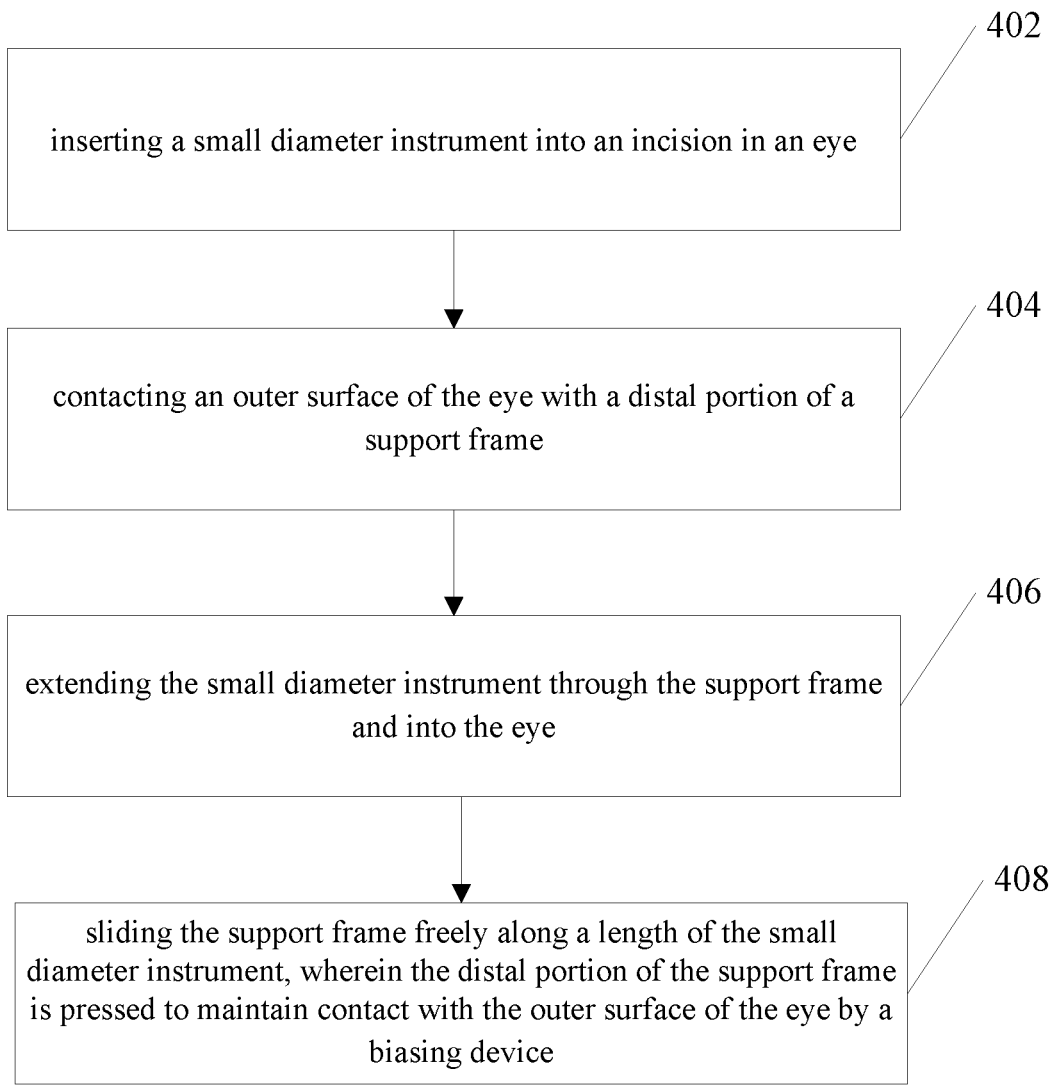
FIG. 4 shows a method of using an instrument according to an embodiment of the invention.

FIG. 4 shows a flow chart of an example method of operating a support device, such as a support device described in examples above. Operation 402 describes inserting a small diameter instrument into an incision in an eye. In operation 404, an outer surface of the eye is contacted with a distal portion of a support frame. In operation 406, the small diameter instrument is extended through the support frame and into the eye. In operation 408, the support frame is slid freely along a length of the small diameter instrument, wherein the distal portion of the support frame is pressed to maintain contact with the outer surface of the eye by a biasing device.

Instruments are shown which diminish the "play" in very small and flexible instruments, such as instruments for vitreous surgery. Embodiment described above include designs where characteristics such as stiffness can be adjusted by the surgeon. Embodiments described above also include adjustments so access is possible to all parts of the vitreous cavity. Embodiments as shown above provide features to make surgical procedures safer. Embodiments described above also increase the variety of cases for which small, more flexible instruments can be used. Although vitreous surgery is discussed above as an example procedure, embodiments of the invention described above and in the following claims are not so limited. Other surgical procedures will also benefit from the advantages that these device configurations provide.

To better illustrate the method and apparatuses disclosed herein, a non-limiting list of embodiments is provided here:

Example 1 includes an ophthalmologic instrument. The instrument includes a base unit having a lateral gripping surface, a small diameter instrument extending from the base unit, the small diameter instrument having a length, a support frame slidably coupled to the small diameter instrument along the length, and a biasing device to urge the support frame towards an extended location along the length of the small diameter instrument. A distal portion of the support frame is adapted to make contact with a patient's eye and wherein a biasing force of the biasing device may be overcome by pressing the distal portion of the support frame against the patient's eye, to extend the small diameter instrument into a posterior portion of the patient's eye when in use.

Example 2 includes the ophthalmologic instrument of example 1, further including one or more supply lines routed through an interior of the base unit to the small diameter instrument.

Example 3 includes the ophthalmologic instrument of any one of examples 1-2, wherein the support frame is spaced apart from the one or more supply lines, and contained completely within the lateral gripping surface.

Example 4 includes the ophthalmologic instrument of any one of examples 1-3, wherein the biasing device includes a spring.

Example 5 includes the ophthalmologic instrument of any one of examples 1-4, wherein the biasing device includes a piston adapted to be biased by pneumatic pressure.

Example 6 includes the ophthalmologic instrument of any one of examples 1-5, wherein the one or more supply lines includes a supply line chosen from a group consisting of fiber optics, media infusion, suction, and drug, or other fluid delivery.

Example 7 includes the ophthalmologic instrument of any one of examples 1-6, wherein the small diameter instrument is chosen from a group consisting of cutting tools, forceps, and scissors.

Example 8 includes the ophthalmologic instrument of any one of examples 1-7, wherein the small diameter instrument includes a vitrectomy blade.

Example 9 includes the ophthalmologic instrument of any one of examples 1-8, wherein the support frame includes a cylinder that fits closely around the small diameter instrument.

Example 10 includes the ophthalmologic instrument of any one of examples 1-9, wherein the small diameter instrument is approximately 23 gauge or smaller in diameter.

Example 11 includes the ophthalmologic instrument of any one of examples 1-10, wherein the small diameter instrument is approximately 25 gauge in diameter.

Example 12 includes the ophthalmologic instrument of any one of examples 1-11, wherein the small diameter instrument is approximately 27 gauge in diameter.

Example 13 includes a method, including inserting a small diameter instrument into an incision in an eye, contacting an outer surface of the eye with a distal portion of a support frame, extending the small diameter instrument through the support frame and into the eye, and sliding the support frame freely along a length of the small diameter instrument, wherein the distal portion of the support frame is pressed to maintain contact with the outer surface of the eye by a biasing device.

Example 14 includes the method of example 13, further including rotating the eye by moving the small diameter instrument against a side of the incision and using the support frame to increase stiffness of the small diameter instrument.

Example 14 includes the method of any one of examples 13-14, further including adjusting a biasing force of the biasing device.

These and other examples and features of the present infusion devices, and related methods will be set forth in part in the above detailed description. This overview is intended to provide non-limiting examples of the present subject matter—it is not intended to provide an exclusive or exhaustive explanation.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ophthalmologic instrument, comprising:
   a base unit having a lateral gripping surface;
   a small diameter instrument extending from the base unit, the small diameter instrument having a length;
   a support frame slidably coupled to the small diameter instrument along the length;
   a biasing device to urge the support frame towards an extended location along the length of the small diameter instrument, wherein a biasing force of the biasing device is adjustable;
   wherein a distal portion of the support frame is adapted to make contact with a patient's eye and wherein a biasing force of the biasing device may be overcome by pressing the distal portion of the support frame against the patient's eye, to extend the small diameter instrument into a posterior portion of the patient's eye when in use; and
   one or more supply lines routed through an interior of the base unit to the small diameter instrument, wherein the support frame is spaced apart from the one or more supply lines, and both the support frame and supply lines are contained laterally within the lateral gripping surface as they pass through the interior of the base unit.

2. The ophthalmologic instrument of claim 1, wherein the biasing device includes a spring.

3. The ophthalmologic instrument of claim 2, further including a screw adjuster to adjust the spring force.

4. The ophthalmologic instrument of claim 1, wherein the biasing device includes a piston adapted to be biased by pneumatic pressure.

5. The ophthalmologic instrument of claim 1, wherein the one or more supply lines includes a supply line chosen from a group consisting of fiber optics, media infusion, suction, and drug, or other fluid delivery.

6. The ophthalmologic instrument of claim 1, wherein the small diameter instrument is chosen from a group consisting of cutting tools, forceps, and scissors.

7. The ophthalmologic instrument of claim 1, wherein the small diameter instrument includes a vitrectomy blade.

8. The ophthalmologic instrument of claim 1, wherein the support frame includes a cylinder that fits closely around the small diameter instrument.

9. The ophthalmologic instrument of claim 1, wherein the small diameter instrument is approximately 23 gauge or smaller in diameter.

10. The ophthalmologic instrument of claim 1, wherein the small diameter instrument is approximately 25 gauge in diameter.

11. The ophthalmologic instrument of claim 1, wherein the small diameter instrument is approximately 27 gauge in diameter.

* * * * *